United States Patent [19]

Werner et al.

[11] Patent Number: 5,619,986
[45] Date of Patent: Apr. 15, 1997

[54] METHOD AND APPARATUS FOR CONTROLLING THE CONCENTRATION OF AT LEAST ONE COMPONENT IN A GAS MIXTURE IN AN ANAESTHETIC SYSTEM

[75] Inventors: Olof Werner, Stadsbudsgatan 10, S-222 36 Lund; Janne Persson, S-242 92 Horby, both of Sweden

[73] Assignee: Olof Werner, Lund, Sweden

[21] Appl. No.: 78,200

[22] PCT Filed: Dec. 23, 1991

[86] PCT No.: PCT/SE91/00904

§ 371 Date: Aug. 18, 1993

§ 102(e) Date: Aug. 18, 1993

[87] PCT Pub. No.: WO92/11887

PCT Pub. Date: Jul. 23, 1992

[30] Foreign Application Priority Data

Jan. 3, 1991 [SE] Sweden .................................. 9100016

[51] Int. Cl.⁶ ............................ A61M 16/10; A62B 7/00; F16K 31/02
[52] U.S. Cl. ................................ 128/204.21; 128/203.12; 128/204.22
[58] Field of Search ........................ 128/203.12, 203.25, 128/205.11, 204.22, 204.21, 204.23

[56] References Cited

U.S. PATENT DOCUMENTS

| | | | |
|---|---|---|---|
| 3,669,134 | 6/1972 | Dobritz | 128/203.25 |
| 4,022,234 | 5/1977 | Dobritz | 128/203.25 |
| 4,150,670 | 4/1979 | Jewett et al. | 128/204.22 |
| 4,345,612 | 8/1982 | Koni et al. | 128/203.25 |
| 4,399,686 | 8/1983 | Kindlund et al. | 73/23 |
| 4,421,113 | 12/1983 | Gedeon et al. | 128/204.23 |
| 4,509,359 | 4/1985 | Gedeon et al. | 128/719 |
| 4,587,967 | 5/1986 | Chu et al. | 128/204.21 |
| 4,702,242 | 10/1987 | Broddner et al. | 128/205.13 |
| 4,770,168 | 9/1988 | Rusz et al. | 128/203.12 |
| 4,903,693 | 2/1990 | Yasue | 128/203.12 |
| 4,905,685 | 3/1990 | Olsson et al. | 128/203.12 |
| 4,989,597 | 2/1991 | Werner | 128/203.12 |
| 5,044,361 | 9/1991 | Werner et al. | 128/203.12 |
| 5,049,317 | 9/1991 | Kiske et al. | 128/203.25 |
| 5,094,235 | 3/1992 | Westenkow et al. | 128/203.12 |
| 5,237,990 | 8/1993 | Psaros et al. | 128/204.21 |
| 5,243,973 | 9/1993 | Falb et al. | 128/203.12 |
| 5,423,313 | 6/1995 | Olsson et al. | |

FOREIGN PATENT DOCUMENTS

| | | | |
|---|---|---|---|
| 0121255 | 9/1988 | European Pat. Off. | 128/204.22 |
| 8806904 | 9/1988 | WIPO | 128/203.12 |

OTHER PUBLICATIONS

Ventilation inhomogeneity during controlled ventilation. Which index should be used? A. Larsson, et al., Journal of Applied Physiology 65 (1988):5, pp. 2030–2039.

"Pulmonary Blood Flow Determination with Selective Rebreathing or $CO_2$", Linnarsson et al., Karolinska Institutet, pp. 39–48.

"Method to Deliver a Preset Inspired Concentration of Anesthetic Regardless of Degree of Rebreathing", Perhag et al., *Anestheslology*, V75, No. 3A, Sep., 1991, A1010.

*Primary Examiner*—Kimberly L. Asher
*Attorney, Agent, or Firm*—Oblon, Spivak, McClelland, Maier & Neustadt, P.C.

[57] ABSTRACT

A reinhalation system for an anesthetic apparatus includes exhalation and inhalation branches which are directly connected to each other. The inhalation branch comprises a dosing unit capable of supplying a component to said inhalation branch. A control unit controls the dosing unit. A first concentration measuring device measuring the concentration of the component and a flow meter measuring a flow rate of a fluid are provided. The dosing unit supplies at least the component to the inhalation branch at a dosing point located downstream of the first concentration meter. The control unit controls the supply of the component as a function of the concentration of the component measured by the concentration meter and the flow rate of the fluid measured by the flow meter.

23 Claims, 2 Drawing Sheets

METHOD AND APPARATUS FOR CONTROLLING THE CONCENTRATION OF AT LEAST ONE COMPONENT IN A GAS MIXTURE IN AN ANAESTHETIC SYSTEM

TECHNICAL FIELD

The present invention relates to an apparatus for controlling the concentration of at least one component in a gas mixture in an anaesthetic system comprising an inhalation branch, a dosing unit for supplying the component, and a control unit for controlling the supply.

Such a device can be employed in inhalation anaesthetics, e.g. for controlling the concentration of the anaesthetic given to the patient in a gas mixture.

The invention also concerns a method for controlling the concentration of at least one component in a gas mixture in an anaesthetic system.

BACKGROUND ART

In the field of anaesthetics, the trend is towards increasingly refined, and thus expensive, anaesthetics. It has consequently become desirable to reduce the consumption thereof.

One way of reducing the consumption of anaesthetics is to use an anaesthetic system with total or partial re-inhalation. In total re-inhalation, no gas escapes from the system, and the patient is breathing essentially the same gas mixture all the time. The carbon dioxide exhaled by the patient is eliminated in a $CO_2$ absorber, and oxygen and the anaesthetic are supplied to maintain the concentrations thereof at the desired level. In partial re-inhalation, only part of the exhaled gas mixture is inhaled again, and a certain amount of fresh gas mixture is instead supplied. The gas surplus is discharged during exhalation. If the consumption of anaesthetics is to be minimized, a system with total re-inhalation is the best option.

Controlling the concentration of anaesthetics in anaesthetic systems with re-inhalation is today often performed manually. The anaesthetist sometimes may consult a gas-concentration meter mounted in the anaesthetic system and serving to measure the concentration of the anaesthetic.

It is also known to control the concentration of the anaesthetic automatically by means of a computer.

WO 88/06904 discloses an apparatus for controlling the concentration of a component in a gas mixture given to the patient. The apparatus includes a patient circuit which consists of a circle system for re-inhalation, which has an inhalation branch and an exhalation branch. A gas-concentration meter for measuring the concentration of the component in the gas mixture is provided in the inhalation branch close to the patient and is connected to a computer. A desired-value transducer for setting the desired concentration of the gas component is also connected to the computer. With the aid of signals from the gas-concentration meter and the desired-value transducer, the computer controls a gas-dosing unit which is provided further away from the patient in the inhalation branch, to give the desired concentration of the gas component. Thus, this is a feedback control.

Both in manual and computer-controlled operation it is, however, difficult to rapidly and highly accurately adjust the concentration of the anaesthetic to the desired level.

This is, among other things, due to the fact that there may be a considerable discrepancy between the concentration of anaesthetic in the flow supplied to the breathing system and the concentration of anaesthetic in the gas mixture inhaled by the patient.

DISCLOSURE OF INVENTION

The object of the present invention is, therefore, to provide an apparatus which enables automatic and highly accurate adjustment to the desired value of the concentration of a component in the gas mixture in an anaesthetic system, there being but a brief time delay.

This object is achieved by an apparatus which is of the type mentioned in the introduction to this specification and which is characterized in that the dosing unit is adapted to supply the component to the inhalation branch at a point located ahead of a gas-concentration meter provided in said branch, and that the control unit is adapted to control the supply of said component as a function of the concentration measured by the gas-concentration meter and the flow rate of the gas mixture in the inhalation branch.

This apparatus enables accurate and rapid control of the concentration of a component in the gas mixture, since the computer, knowing the flow rate of the gas mixture in the inhalation branch and the concentration of the component in the gas mixture before the dosing point, can determine the flow rate of the supplied component needed to give the desired concentration. Thus, this is a feed forward control.

If the flow rate in the inhalation branch is unknown, it is conveniently measured by a flow meter provided e.g. in the inhalation branch.

The dosing unit is advantageously disposed downstream from the flow meter in the inhalation branch, so that the flow meter measures the flow rate of the gas mixture before the dosing point.

The dosing point and the concentration meter are preferably arranged close to one another. The volume contained by the anaesthetic system between the these two components should not exceed 2 l, and should preferably not be higher than 200 ml. By arranging the two components close to one another, a high-speed device is obtained, which is able to compensate for variations in the concentration of the component in the re-inhaled gas mixture, so that the desired inhaled concentration is maintained.

The flow meter, the gas-concentration meter and the dosing unit are advantageously arranged in one and the same unit, which simplifies mounting in the anaesthetic system. This unit should be mounted at a distance from the patient, to prevent the measuring devices from being affected by phlegm, moisture and the like emanating from the patient.

The apparatus may include an additional gas-concentration meter for measuring the concentration of the component downstream from the dosing point. This gas-concentration meter may perform a monitoring function, guarding against too high a discrepancy between the desired and the obtained concentration of the component in the gas mixture in the inhalation branch, or form part of a feedback circuit for refining the control.

The above apparatus can be employed in open anaesthetic systems, as well as in anaesthetic systems with total or partial re-inhalation. The greatest advantages are, however, obtained with re-inhalation systems. In addition, the apparatus is applicable to anaesthetic systems with spontaneous or controlled breathing.

The invention also concerns a method for performing the control, which has the distinctive features recited in the appended claims.

BRIEF DESCRIPTION OF THE DRAWINGS

The invention will be described in more detail below with reference to preferred embodiments and the accompanying drawings, in which FIG. 1 schematically illustrates the position of an apparatus according to the invention in an anaesthetic system with re-inhalation.

BEST MODES OF THE INVENTION

Figure 1:
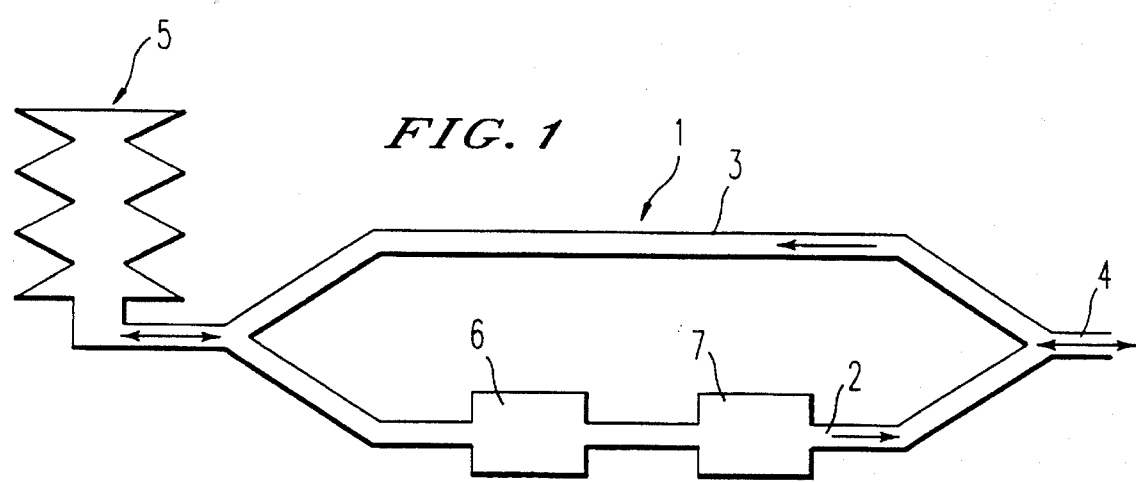

FIG. 1 schematically illustrates an anaesthetic system 1 for re-inhalation, which comprises an inhalation branch 2, an exhalation branch 3, a patient's breathing element 4 and a pair of bellows 5. In the inhalation branch 2 is mounted a $CO_2$ absorber 6 and a device 7 for controlling the concentration of a component, e.g. an anaesthetic, in the gas mixture circulating in the anaesthetic system. There is also provided a device for supplying fresh gas (not shown).

The gas mixture in the anaesthetic system flows in the directions indicated by the arrows. In the inhalation branch 2 and the exhalation branch 3, there is a one-way flow, whereas there is a two-way flow in the patient's element 4 and the piece connecting the inhalation and exhalation branches to the pair of bellows 5.

Figure 2:
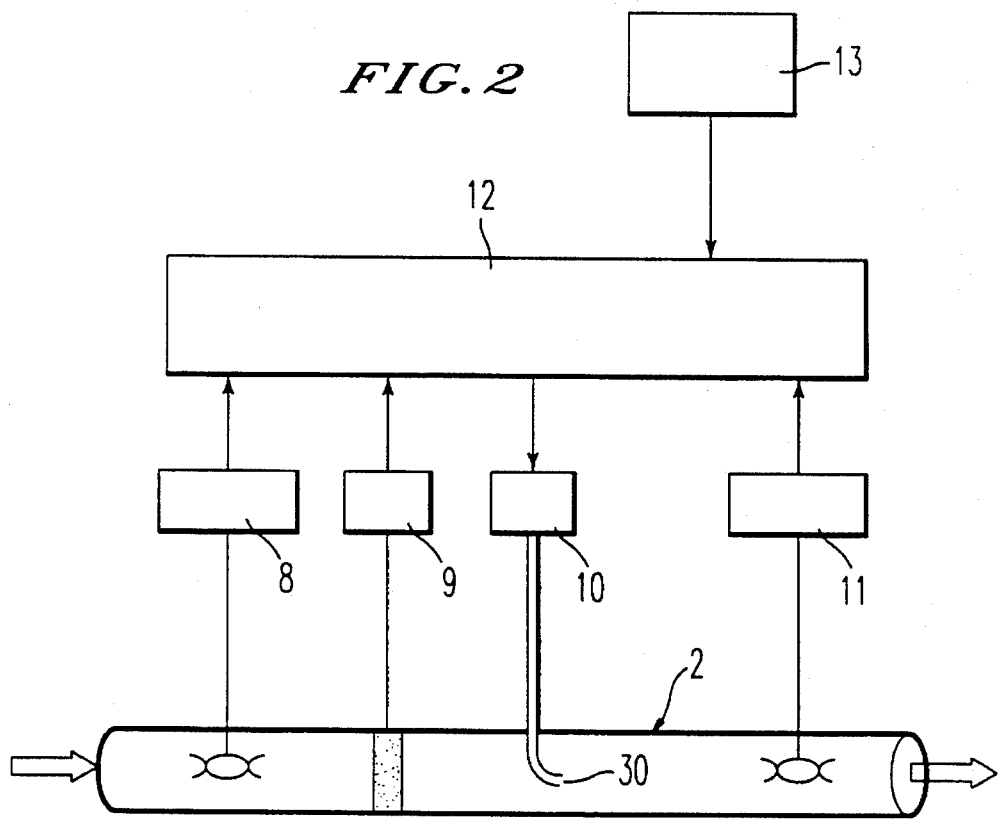
FIG. 2 is a basic diagram illustrating the invention.

FIG. 2 is a basic diagram illustrating an apparatus according to the invention. The apparatus includes a first gas-concentration meter 8 adapted to measure the concentration of the anaesthetic in the gas mixture in the inhalation branch 2 (of which only a part is shown in the Figure); a flow meter 9 adapted to measure the flow rate of the gas mixture in the inhalation branch 2; a dosing unit 10 adapted to supply the anaesthetic at a dosing point 30 in the inhalation branch 2; and additional concentration meter 11 also adapted to measure the concentration of the anaesthetic in the gas mixture; a desired-value transducer 13 serving to set the desired concentration of the anaesthetic in the gas mixture for inhalation; and a control unit 12 adapted to receive input signals from the concentration meter 8, the flow meter 9, the concentration meter 11 and the desired-value transducer 13, as well as to calculate and transmit a control signal to the dosing unit 10.

The concentration meter 8 and the flow meter 9 are provided upstream from the dosing point 30, and are, in other words, located further away from the patient than is the dosing point 30. The concentration meter 8 and the flow meter 9 thus measure the concentration of the anaesthetic and the flow rate of re-inhaled gas. The relative positions of the concentration meter 8 and the flow meter 9 are without interest.

The apparatus illustrated in FIG. 2 operates as follows. The anaesthetist sets the desired concentration of the anaesthetic in the inhalation gas by means of the desired-value transducer 13 which transmits to the control unit 12 an input signal to this effect. The control unit 12 receives input signals from the concentration meter 8 and the flow meter 9, and is thus able to determine the flow rate at which the anaesthetic is to be supplied to the inhalation branch by the dosing unit 10, according to the following formula:

$$V_v = V_i \cdot (C_i - C_r)/(100 - C_i) \tag{1}$$

wherein $V_v$ is the flow rate at which the anaesthetic is to be supplied to the inhalation branch, $V_i$ is the flow rate of re-inhaled gas mixture in the inhalation branch, $C_i$ is the desired concentration in per cent of the anaesthetic in the inhalation branch, and $C_r$ is the concentration of the anaesthetic in the re-inhaled gas mixture.

This simple control algorithm adjusts itself automatically to any changes in the ventilation pattern or the degree of re-inhalation. In addition, it responds rapidly when the desired concentration of anaesthetic is altered.

The concentration meter 8 and the dosing point 30 are advantageously located close to one another. The volume therebetween in the inhalation branch should not exceed 2 l, preferably not 200 ml, so that the anaesthetic is supplied in the flow in which a corresponding measuring of the concentration has been effected.

The additional concentration meter 11 is not essential to the function of the apparatus. This meter is disposed downstream from the dosing point 30, and is used for measuring the obtained concentration of the anaesthetic. It may serve as a safety device, guarding against too high a discrepancy between the desired and the obtained concentration of the anaesthetic. It might also be employed in a feedback method for refining the feed forward control.

It should also be pointed out that there is no need for the flow meter 9 if the flow rate of the gas mixture in the inhalation branch is known, and that it suffices to transmit the flow rate value in the form of an input signal to the control unit 12.

Figure 3:
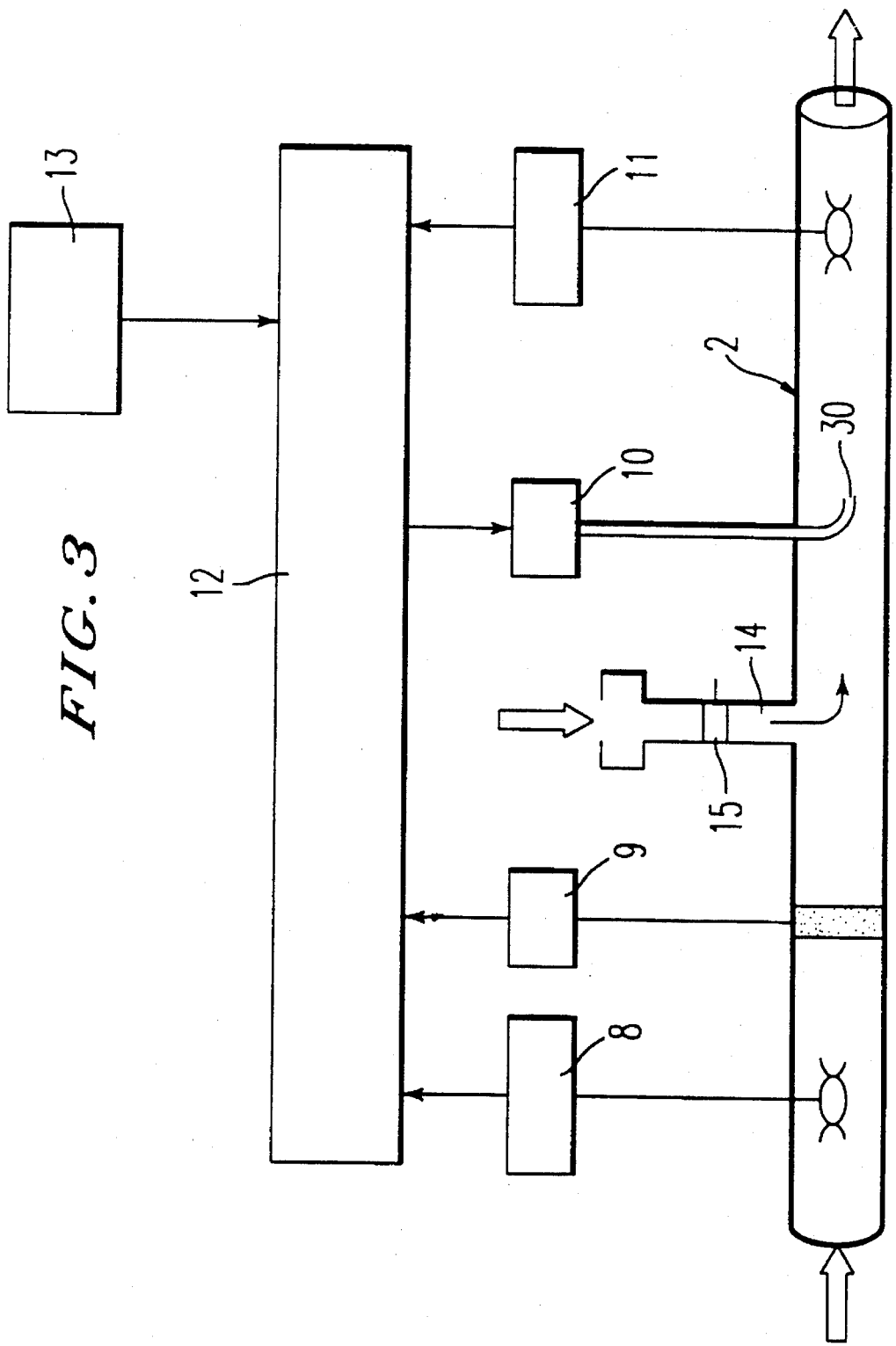
FIG. 3 is a basic diagram illustrating the invention, in which the flow rate of the fresh gas mixture supplied is measured.

FIG. 3 corresponds to FIG. 2, excepting an inlet 14 for supplying $O_2$ and $N_2O$/air from conventional rotameters. A flow meter 15 adapted to measure the flow rate of $O_2$ and $N_2O$/air is mounted in the inlet 14.

In operation, the anaesthetist manually adjusts the flow rate of $O_2$ and $N_2O$/air by means of the rotameters. The control unit 12 determines the flow rate $V_v$ at which the anaesthetic is to be supplied, according to the following formula:

$$V_v = V_i \cdot (C_i - C_r)/(100 - C_i) + V_{rot} \cdot C_i/(100 - C_i) \tag{2}$$

wherein $V_{rot}$ represents the flow rate measured by the flow meter 15.

Since the calibration of the flow meter can vary, depending e.g. on the concentration of oxygen, a concentration meter (not shown) is conveniently arranged in the inlet 14 or in the inhalation branch 2 for measuring the oxygen concentration and transmitting a signal to the control unit 12.

The inlet 14 is preferably provided downstream from the concentration meter 8 and the flow meter 9, for the following reason. During the exhalation phase, the flow of re-inhaled gas in the inhalation branch 2 is essentially non-existent. There is, however, obtained a flow from the rotameter in to the inhalation branch 2, via the inlet 14. If this flow from the rotameter is supplied before the concentration meter 8, the concentration of anaesthetic measured by this meter will vary to a greater extent than if the flow is supplied ahead of the concentration meter.

Since concentration meters are fairly slow, they should preferably measure a slowly varying signal.

The supply of oxygen and $N_2O$/air may also be automatic. If so, the anaesthetist sets the desired concentration of oxygen or $N_2O$ or nitrogen gas by means of the is then performed in the manner described above in connection with the control of the concentration of anaesthetic. It goes without saying that the concentration meter 8 then has to be able to measure the concentrations of these substances.

EXAMPLE

The device shown in FIG. 2 was tested in an anaesthetic system connected to a test lung. The concentration meters 8, 11 employed were commercially available anaesthetic-gas meters, and the flow meter 9 was a pneumotachograph connected to a differential-pressure transducer. The control unit 12 employed was a computer connected to the concentration-meters 8, 11, the flow meter 9 and the dosing unit 10 via analog inputs and outputs. The anaesthetist selected the desired concentration of isoflurane (an anaesthetic). The flow rate at which isoflurane was to be supplied was determined according to formula (1) above. The isoflurane was dosed in the form of a highly concentrated gas mixture with a content of about 40% of air/oxygen. The supply rate was modulated by supplying the highly concentrated isoflurane mixture in brief (0.1 s), equal pulses with a frequence proportionate to the isoflurane flow rate determined by the control algorithm in the control unit 12. The resulting inhaled isoflurane concentration was measured by means of the gas-concentration meter 11. A mixing volume was placed between the dosing point 30 and the additional concentration meter 11 to compensate for the fact that the pulses of isoflurane gas were not infinitely small.

The apparatus according to the invention was connected in an almost closed system whose fundamental features are described in Anaesthesia 45, pp 855–858, 1990.

In addition to isoflurane, minimal amounts of other gases were supplied to the anaesthetic system to keep this as closed as possible. The system was operated by a ventilator having a volume per minute of 6.0 l. This test was also performed in an open system operated by a ventilator. The desired isoflurane concentration was set at 1% in both tests, and the resulting concentration was within ±0.1% of the desired concentration within 30 s in both tests. In the tests, which took 1 h, 30 g isoflurane was used up in the open system and less than 5 g was used up in the practically closed system.

In another test, the desired isoflurane concentration was varied between 0.5% and 2.0%. The resulting concentrations were as desired.

The same excellent results have also been obtained in experiments with animals.

To conclude, the invention makes it possible to control the amount of anaesthetic in a simple manner, so as to obtain the desired concentration in the inhalation gas. The control is independent of the degree of re-inhalation, which is continuously measured and compensated for by the control unit. Since the control system is of simple construction, the technical safety is satisfactory. The fact that the entire equipment can be arranged as a unit in the inhalation branch of the anaesthetic system and be stationarily mounted on the anaesthetic trolley also contributes to the safety. In operation, the anaesthetist communicates with the control system in the simplest possible way: the desired inhaled concentration of anaesthetic, optionally also of oxygen, is indicated.

INDUSTRIAL APPLICABILITY

The invention is applicable to the control of all the gas components in the anaesthetic system, i.e. anaesthetics as well as oxygen and air/nitrogen gas. Thus, the invention may be utilized also for lowering the concentration of anaesthetic in the inhalation gas, which is performed by increasing the concentrations of the other gas components.

We claim:

1. A reinhalation system of an anesthetic apparatus, comprising a breathing element of a patient;

a ventilating source;

an exhalation branch and an inhalation branch, said exhalation and inhalation branches being directly connected to each other and each of said exhalation and inhalation branches interconnecting said ventilating source with said breathing element;

a gas mixture containing at least a first component, said first component being at least partially introduced into said inhalation system at said inhalation branch;

said inhalation branch being located downstream of said ventilating source and comprising a dosing unit supplying said first component to said inhalation branch, a control unit including a computer controlling said dosing unit, a first gas-concentration meter provided in the inhalation branch and measuring the concentration of said first component in the inhalation branch, a flow meter located in the inhalation branch, said flow meter determining a flow rate of said gas mixture in the inhalation branch, said dosing unit supplying at least said first component to said inhalation branch at a dosing point located downstream of said first concentration meter, said control unit controlling said supply of said first component as a function of the concentration of said first component measured by said first concentration meter and the flow rate of the gas mixture measured by said flow meter;

a feed forward control system which includes said flow meter located in said inhalation branch upstream of said dosing point and said gas concentration meter wherein said gas concentration meter is located upstream of said dosing point, said flow meter and said gas concentration meter generating/sending signals to said computer, wherein said computer is responsive to signals received from said flow meter and gas concentration meter and said computer determines a required gas flow rate to achieve a desired gas concentration for patient delivery; and an adjustment mechanism achieving high-speed gas concentration adjustments which comprises said dosing point and said gas concentration meter being positioned very close together such that the volume of gas and the system between said dosing point and said gas concentration meter are minimized;

wherein said rate of flow of the gas mixture and concentration of said first component in said inhalation branch vary with breathing of a patient into said breathing element.

2. The reinhalation system of claim 1, wherein said first component is an anesthetic.

3. The reinhalation system of claim 2, further comprising an inlet for supplying a fresh gas mixture, said inlet is disposed in said inhalation branch downstream of said first concentration meter, so that said control unit further controls supply of said anesthetic as a function of a flow rate of said fresh gas mixture.

4. The reinhalation system of claim 1, wherein said dosing unit supplies said first component to said inhalation branch at said dosing point located downstream of said flow meter.

5. The reinhalation system of claim 1, wherein said first concentration meter, said flow meter and said dosing unit are combined in a single unit mountable at said inhalation branch.

6. The reinhalation system of claim 1, further comprising a second concentration meter measuring the concentration of said first component within said inhalation branch downstream of said dosing point.

7. A reinhalation system as claimed in claim 1, wherein a volume contained by the inhalation tube between the dosing point and the concentration meter is not greater than 2 liters.

8. A reinhalation system of an anesthetic apparatus, comprising an exhalation branch and an inhalation branch, said exhalation and inhalation branches being directly connected to each other;

a gas mixture containing at least a first component, said first component being at least partially introduced into said inhalation system at said inhalation branch;

said inhalation branch comprising a dosing unit for at least partially supplying said first component to said inhalation branch, a control unit controlling said dosing unit, a first gas-concentration meter measuring the concentration of said first component in the inhalation branch, a flow meter determining a flow rate of said gas mixture in the inhalation branch, said dosing unit supplying at least said first component to said inhalation branch at a dosing point located downstream of said first concentration meter, said control unit controlling said supply of said first component as a function of the concentration of said first component measured by said first concentration meter and the flow rate of the gas mixture measured by said flow meter; wherein said rate of flow of the gas mixture and concentration of said first component in said inhalation branch vary with breathing of a patient, said dosing unit supplies said component to said inhalation branch at said dosing point located downstream of said flow meter and wherein a volume of said inhalation branch between said first concentration meter and said dosing point is less than 200 ml.

9. A reinhalation system of an anaesthetic apparatus, comprising a ventilating source;

an exhalation branch and an inhalation branch, said exhalation and inhalation branches being directly connected to each other and each of said exhalation and inhalation branches interconnecting said ventilating source with said breathing element;

said inhalation branch being located downstream of said ventilating source and comprising a dosing unit supplying a component to said inhalation branch, a control unit including a computer controlling said dosing unit, a first concentration meter provided in the inhalation branch and measuring the concentration of said component in the inhalation branch, a flow meter located in the inhalation branch, said flow meter determining a flow rate of a fluid in the inhalation branch, said dosing unit supplying at least said component to said inhalation branch at a dosing point located downstream of said first concentration meter and said control unit controlling said supply of said component as a function of the concentration of said component measured by said first concentration meter and the flow rate of the fluid measured by said flow meter;

a feed forward control system which includes said flow meter located in said inhalation branch upstream of said dosing point and said gas concentration meter wherein said gas concentration meter is located upstream of said dosing point, said flow meter and said gas concentration meter generating/sending signals to said computer, wherein said computer is responsive to signals received from said flow meter and gas concentration meter and said computer determines a required gas flow rate to achieve a desired gas concentration for patient delivery; and an adjustment mechanism achieving high-speed gas concentration adjustments which comprises said dosing point and said gas concentration meter being positioned very close together such that the volume of gas and the system between said dosing point and said gas concentration meter are minimized;

wherein said rate of flow of said fluid and concentration of said component vary with breathing of a patient into said breathing element.

10. The reinhalation system of claim 9 wherein said fluid is a gas mixture containing said component.

11. The reinhalation system of claim 10, wherein said component is an anaesthetic.

12. The reinhalation system of claim 10, wherein said dosing unit supplies said component to said inhalation branch at said dosing point located downstream of said flow meter.

13. The reinhalation system of claim 10, wherein said first concentration meter, said flow meter and said dosing unit are combined in a single unit mountable at said inhalation branch.

14. The method of claim 13, wherein said first component is an anesthetic.

15. The method of claim 13, wherein in said step "3" the dosing unit supplies said first component to said inhalation branch at a dosing point located downstream of said first concentration meter.

16. The method of claim 15, wherein in said step "3" the dosing unit supplies said first component to said inhalation branch at the dosing point located downstream of said flow meter.

17. The reinhalation system of claim 10, further comprising a second concentration meter measuring the concentration of said component downstream of said dosing point.

18. A reinhalation system as claimed in claim 9, wherein a volume contained by the inhalation tube between the dosing point and the concentration meter is not greater than 2 liters.

19. A reinhalation system of an anaesthetic apparatus, comprising:

a ventilation source;

a breathing element for a patient;

an exhalation branch and an inhalation branch, said exhalation and inhalation branches being directly connected to each other and interconnecting said breathing element with said ventilating source;

said inhalation branch comprising a dosing unit supplying a component to said inhalation branch, a control unit controlling said dosing unit, a first concentration meter provided in the inhalation branch and measuring the concentration of said component in the inhalation branch, a flow meter determining a flow rate of a fluid in the inhalation branch, said dosing unit supplying at least said component to said inhalation branch at a dosing point located downstream of said first concentration meter, said control unit controlling said supply of said component as a function of the concentration of said component measured by said first concentration meter and the flow rate of the fluid measured by said flow meter;

wherein said rate of flow of said fluid and concentration of said component vary with breathing of a patient into said breathing element, said fluid comprises a gas mixture containing said component, said dosing unit supplies said component to said inhalation branch at said dosing point located downstream of said flow meter and wherein a volume of said inhalation branch between said first concentration meter and said dosing point is less than 200 ml.

20. A method of supplying a patient with a gas mixture having at least a first component through a reinhalation system of an anaesthetic apparatus, comprising:

a ventilating source;

a breathing element of a patient;

an exhalation branch and an inhalation branch, said exhalation and inhalation branches being directly connected to each other and interconnecting said breathing element with said inhalating source, said inhalation branch including a dosing unit supplying at least said first component to a dosing point in said inhalation branch, a control unit including a computer controlling said dosing unit, a first gas concentration meter provided upstream of said dosing point in the inhalation branch measuring a concentration of said first component in the inhalation branch and a flow meter determining a flow rate of said gas mixture in the inhalation branch; wherein said method comprises the steps of:

providing a feed forward control system which includes said flow meter and said gas concentration meter, said flow meter and gas concentration meter generating/sending signals to said computer;

said computer being responsive to said flow meter and said gas concentration meter signals and determining a required gas flow rate to achieve a desired gas concentration for patient delivery; and achieving high-speed gas concentration adjustments by positioning said dosing point and said gas concentration meter very close together such that the volume of gas in the system between said gas dosing point and said concentration meter are minimized.

21. The method of claim 20, wherein a rate of delivery of said first component to said inhalating branch is determined according to the following formula:

$$V_V = V_i \cdot (C_i - C_r)/(100 - C_i)$$

wherein $V_V$ is the flow rate of delivery of said first component to said inhalation branch;

$V_i$ is the flow rate of the gas mixture, $C_i$ is a desired concentration in percents of said first component in the gas mixture, and $C_r$ is a measured concentration of said first component in percents of said mixture.

22. The method of claim 20, wherein said inhalation branch further comprising a second concentration meter, said second concentration meter measures concentration of said first component within said inhalation branch downstream of said dosing point.

23. The method of claim 22, wherein said first and second concentration meters are gas-concentration meters.

* * * * *

UNITED STATES PATENT AND TRADEMARK OFFICE
CERTIFICATE OF CORRECTION

PATENT NO. : 5,619,986
DATED : APRIL 15, 1997
INVENTOR(S) : Olof WERNER ET AL

It is certified that error appears in the above-identified patent and that said Letters Patent is hereby corrected as shown below:

Column 7, line 13, change "tube" to --branch--.

Column 8, line 36, change "13" to --20--;

line 38, change "13" to --20--;

line 50, change "tube" to --branch--.

Column 10, line 1, before "providing" insert --(1)--;

line 5, before "said" (first occurrence) insert --(2)--;

line 9, before "achieving" insert --(3)--.

Signed and Sealed this

Twelfth Day of May, 1998

Attest:

BRUCE LEHMAN

Attesting Officer

Commissioner of Patents and Trademarks